United States Patent [19]

Pews et al.

[11] 4,211,873
[45] Jul. 8, 1980

[54] PREPARATION OF CHLOROMETHYLPYRIDINES

[75] Inventors: R. Garth Pews; Mezzie L. Ash, both of Midland, Mich.

[73] Assignee: The Dow Chemical Company, Midland, Mich.

[21] Appl. No.: 927,718

[22] Filed: Jul. 25, 1978

[51] Int. Cl.$^2$ .......................................... C07D 213/26
[52] U.S. Cl. .................................................. 546/346
[58] Field of Search ...................... 260/290 HL, 290 P; 546/346

[56] References Cited

U.S. PATENT DOCUMENTS 3,123,608  3/1964  Mathes et al. ...................... 260/283

OTHER PUBLICATIONS

Abramovitch, Pyridine and Derivatives, Supplement Part Two, John Wiley and Sons, p. 457.
Kato, Chem. Abstracts, vol. 50, (12)8665, Jun. 25, 1956.

*Primary Examiner*—Alan L. Rotman
*Attorney, Agent, or Firm*—Joyce P. Hill; L. Wayne White

[57] ABSTRACT

Monochloromethylpyridines are produced by reacting 2- or 4-methylpyridine oxides with phosphoryl chloride in the presence of an organic base. One product, 2-chloromethylpyridine, is formed by reacting 2-picoline-N-oxide with phosphoryl chloride in the presence of triethylamine.

7 Claims, No Drawings

PREPARATION OF CHLOROMETHYLPYRIDINES

BACKGROUND OF THE INVENTION

1. Field of the Invention

This invention pertains to the monochlorination of methyl groups on pyridine oxides.

2. Description of the Prior Art

Although monochloromethylpyridines are a well-known class of compounds, the most useful member is 2-chloromethylpyridine. A variety of processes have been used to prepare these compounds.

Chloromethylpyridine compounds have been formed by the reaction of pyridine oxide compounds with certain chlorinating agents. The usual means of chlorinating pyridine oxide is with phosphorus pentachloride or phosphoryl chloride, resulting in a mixture of 2- and 4-chloromethylpyridines. Another process is the direct chlorination of 2-picoline, but the product is contaminated by di- and trichloromethylpyridines.

T. Kato described the reaction of α-picoline-1-oxide with phosphoryl chloride in Yakugaku Zasshi, 75, 1239 (1955) C.A. 50:8,665h (1956). The reaction was run neat at temperatures of 100° C.–140° C. After removing the phosphoryl chloride, the residue was neutralized with potassium carbonate and extracted with ethyl ether. Only trace amounts of 2-chloromethylpyridine were obtained.

E. Matsumura, J. Chem. Soc. (Japan) 74,363 (1953) C.A. 48:6,422b (1954), described the formation of monochloromethylpyridines from the reaction of 2-picoline-1-oxide with p-toluenesulfonyl chloride.

Mathis et al. (U.S. Pat. No. 3,123,608) described a process for chlorinating side-chain groups by reacting methylpyridines with chlorine. Stepwise chlorination to mono-, di- and trichloromethyl derivatives depended upon the following conditions: (1) reaction temperature between 40° C. and 80° C., (2) inert diluent as a solvent, and (3) an inorganic hydrochloric acid binding agent. However, the yield of 2-picolyl chloride obtained from this process was only 65 percent of theory. Di- and trichloromethylpyridine were also formed by contaminating by-products.

Side-chain chlorination of methylpyridines was discussed by Hattori et al. in Japanese Patent No. 74 127,977; C.A. 84:121,665p (1975). Water and a hydrochloric acid acceptor were present in an inert solvent. The compound 2-picoline was chlorinated to 2-(chloromethyl) and 2-(dichloromethyl) pyridine following this process.

SUMMARY OF THE INVENTION

Our novel process comprises the formation of monochloromethylpyridines by the reaction of a 2- or 4-methylpyridine oxide with phosphoryl chloride in the presence of an organic base. The products are produced in excellent yields at commercially satisfactory reaction rates. The reaction proceeds at lower temperatures and shorter reaction times than previous methods.

DETAILED DESCRIPTION OF THE INVENTION

The 2- or 4-methylpyridine oxides utilized in this process as reactants form a known class of compounds. Members of this class of compounds are aromatic amines having a nitrogen atom in the aromatic nucleus (ring structure), which is present as an amine oxide. Examples of such suitable aromatic amine oxides include the picoline-N-oxides, the quinoline oxides, and the like, bearing methyl groups in the 2- or 4-ring position, relative to the ring nitrogen. These compounds can also bear one or more inert substituents; i.e., substituents that are inert in the process. The following tables illustrate a variety of members in the class of 2- or 4-methylpyridine oxides; however, 2-picoline-N-oxide is the preferred reactant.

TABLE I

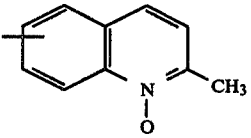

| X | Y | Z |
|---|---|---|
| H | H | H |
| Br | H | H |
| H | $CH_3$ | H |
| $C_2H_5$ | $C_6H_6$ | Cl |
| F | H | $C_2H_4O$ |

TABLE II

| X | Y |
|---|---|
| H | H |
| H | Cl |
| Br | Br |
| $C_6H_6$ | H |
| $C_2H_4O$ | Cl |

TABLE III

X = Cl, Br, F, $C_6H_6$, $CH_3$, $C_2H_5$, $C_6H_5Cl$, $C_2H_4O$

TABLE IV

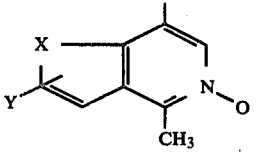

| X | Y | Z |
|---|---|---|
| S | Cl | $CH_3$ |
| O | $C_2H_5$ | $C_6H_5CH_2Cl$ |
| O | $C_6H_6$ | Br |
| S | $C_2H_4O$ | $C_6H_5Cl$ |
| S | $(CH_3)_2CH$ | F |

Inert organic chlorinated hydrocarbons are normally used as the reaction solvent. These chlorinated hydrocarbons include methylene chloride, chloroform, carbon tetrachloride, ethylene dichloride, tetrachloroethylene, perchloroethylene, methyl chloroform, and the like.

An organic base, preferably a tertiary amine, is used to increase the yield of the monochloromethyl product. In particular, nitrogen bases are preferred, especially tri(lower alkyl)amines, such as triethylamine and trimethylamine.

Any sequence for adding the reagents can be utilized in this process, but product yields are generally maximized by adding the phosphoryl chloride incrementally to the 2-picoline-N-oxide in the reaction solvent with thorough blending. The organic base can be added to the reaction mixture initially or after a portion (e.g., 10 percent) of the phosphoryl chloride has been added.

The reaction temperature is normally maintained from about 40° C. to about 80° C., preferably from about 40° C. to about 50° C.

At least an equimolar amount of phosphoryl chloride is needed to react with the 2- or 4-methylpyridine oxide based on the stoichiometry of the reaction. This stoichiometric ratio of reactants is normally used.

Agitation (e.g., stirring, swirling, etc.) of the reaction mixture is advantageous.

The following examples further illustrate the invention. These examples are illustrations only and are not limiting on the process.

EXAMPLE 1

To a stirred solution of 1.4 g (9.17 mmol) of phosphoryl chloride in 5 ml of perchloroethylene was added 1.85 g (18.3 mmol) of triethylamine. To the resulting solution at 0° C. was added a solution of 1.00 g (9.17 mmol) of 2-picoline-N-oxide in 5 ml of perchloroethylene. After the addition, the solution was heated at 100° C. for 3 hours and overnight at room temperature. A saturated solution of sodium bicarbonate was added until the aqueous layer remained basic. The aqueous layer was extracted with six portions of chloroform, the combined organic layers were dried with sodium sulfate and the solvent removed in vacuo to give 0.84 g of crude 2-chloromethylpyridine or a 71 percent yield. Vapor phase chromatography analysis on UCW 98 (⅛"×4') temperature programmed 78° C.–150° C. at 6° C./min showed the product to be greater than 95 percent pure.

EXAMPLE 2

Equimolar amounts (0.0092 mole) of 2-picoline-N-oxide, phosphoryl chloride, and triethylamine were reacted in chloroform and the reagents were stirred at room temperature for 30 minutes. The chloroform was removed and the remaining solution was heated at 70° C. for 3 hours. An 88 percent yield of 2-chloromethylpyridine was produced.

EXAMPLE 3–7

Each example was performed in a similar manner as Example 1 and the amounts of reagents and results are shown in Table V.

TABLE V

| Example | 2-Picoline--N-oxide (moles) | POCl$_3$ (moles) | Solvent | Triethylamine (moles) | Product Yield (percent of theory) | Conditions |
|---|---|---|---|---|---|---|
| 3 | 0.0092 | 0.0092 | CHCl$_3$ | 0.0184 | 94 | Reflux in CHCl$_3$ |
| 4 | 0.0092 | 0.0092 | Perc[1] | 0.0184 | 97 | N-oxide compound added to a mixture of TEA[3] & POCl$_3$; cooled to 100° C. |
| 5 | 0.0092 | 0.0092 | Perc | 0.0184 | 95 | POCl$_3$ added to TEA/N-oxide; 100° C. |
| 6 | 0.0137 | 0.0137 | Perc | 0.0184 | 93 | N-oxide compound added to TEA/POCl$_3$ |
| 7 | 0.0137 | 0.0137 | EDC[2] | 0.0184 | 95 | N-oxide compound added to TEA/POCl$_3$; 70° C. |

[1] Perc = perchloroethylene
[2] EDC = ethylene dichloride
[3] TEA = triethylamine

EXAMPLE 8

A reaction was run in which a solution of phosphoryl chloride was added dropwise to the solution of 2-picoline-N-oxide. After approximately 10 percent of the phosphoryl chloride solution had been added to the organic base, triethylamine was added dropwise. The reaction was maintained at 45° C. Using this method a yield of 2-chloromethylpyridine of 90 percent was obtained. The amounts used were: 0.0083 mole of 2-picoline-N-oxide, 0.00916 mole of phosphoryl chloride and 0.00916 mole of triethylamine. Methylene chloride was used as the solvent.

We claim:

1. A process for preparing 2- or 4-chloromethylpyridine comprising reacting by contacting a 2- or 4-methylpyridine-N-oxide with phosphoryl chloride in the presence of an organic base and an inert halogenated hydrocarbon solvent at a temperature between about 40° C. to about 80° C.

2. The process of claim 1 wherein said pyridine compound is 2-picoline-N-oxide.

3. The process of claim 1 wherein said organic base is a tri(lower alkyl)amine.

4. The process of claim 3 wherein said tri(lower alkyl) amine is triethylamine.

5. The process of claim 1 where the reaction is run in an inert solvent.

6. The process of claim 5 wherein said solvent is methylene chloride, chloroform, carbon tetrachloride, methyl chloroform, perchloroethylene, ethylene dichloride, or tetrachloroethylene.

7. The process of claim 5 wherein said pyridine compound is 2-picoline-N-oxide, said organic base is triethylamine, said solvent is methylene chloride, and the temperature is 45° C.

* * * * *